United States Patent [19]

Harsany

[11] 4,337,041
[45] Jun. 29, 1982

[54] DENTAL WEDGE

[76] Inventor: John D. Harsany, 1 Marion Ave., Mansfield, Ohio 44903

[21] Appl. No.: 191,842

[22] Filed: Sep. 29, 1980

[51] Int. Cl.³ .............................................. A61C 7/00
[52] U.S. Cl. ................................................... 433/149
[58] Field of Search ...................................... 433/149

[56] References Cited

U.S. PATENT DOCUMENTS

| 442,107 | 9/1890 | Davison | 433/149 |
| 2,629,930 | 3/1953 | Lane | 433/149 |
| 3,890,714 | 6/1975 | Gores | 433/149 |

FOREIGN PATENT DOCUMENTS 340485 4/1935 Italy .................................. 433/149

Primary Examiner—Robert Peshock
Attorney, Agent, or Firm—Samuel Louis Sachs

[57] ABSTRACT

A dental wedge, for interproximal insertion in the interdental space between teeth for fixing a matrix band in position, including depressions in the lateral surfaces thereof for positively engaging the teeth and locking the wedge therebetween. Means are also provided for simulating the contour of the concave bulbous papillia of the gingiva disposed in the interdental space when the matrix band is affixed about the tooth and the wedge is interproximally positioned.

12 Claims, 8 Drawing Figures

U.S. Patent     Jun. 29, 1982     4,337,041
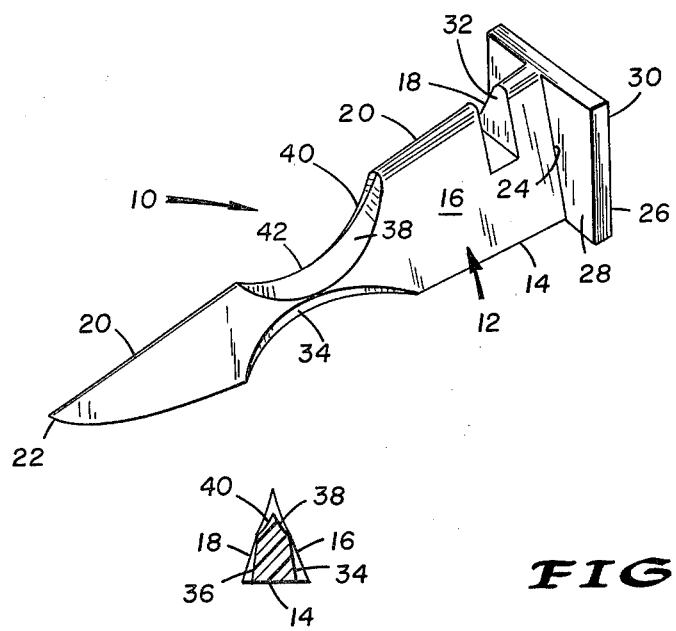
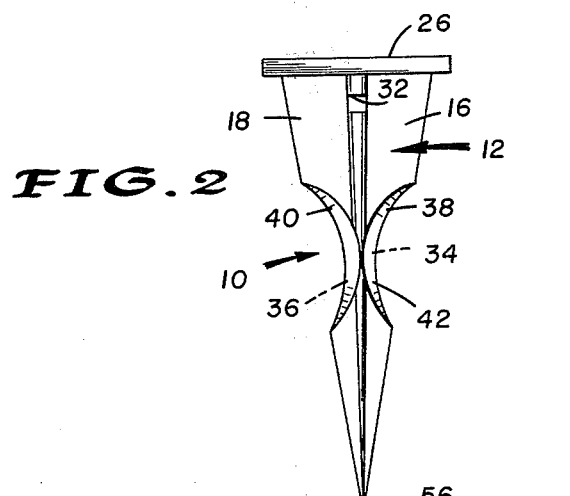
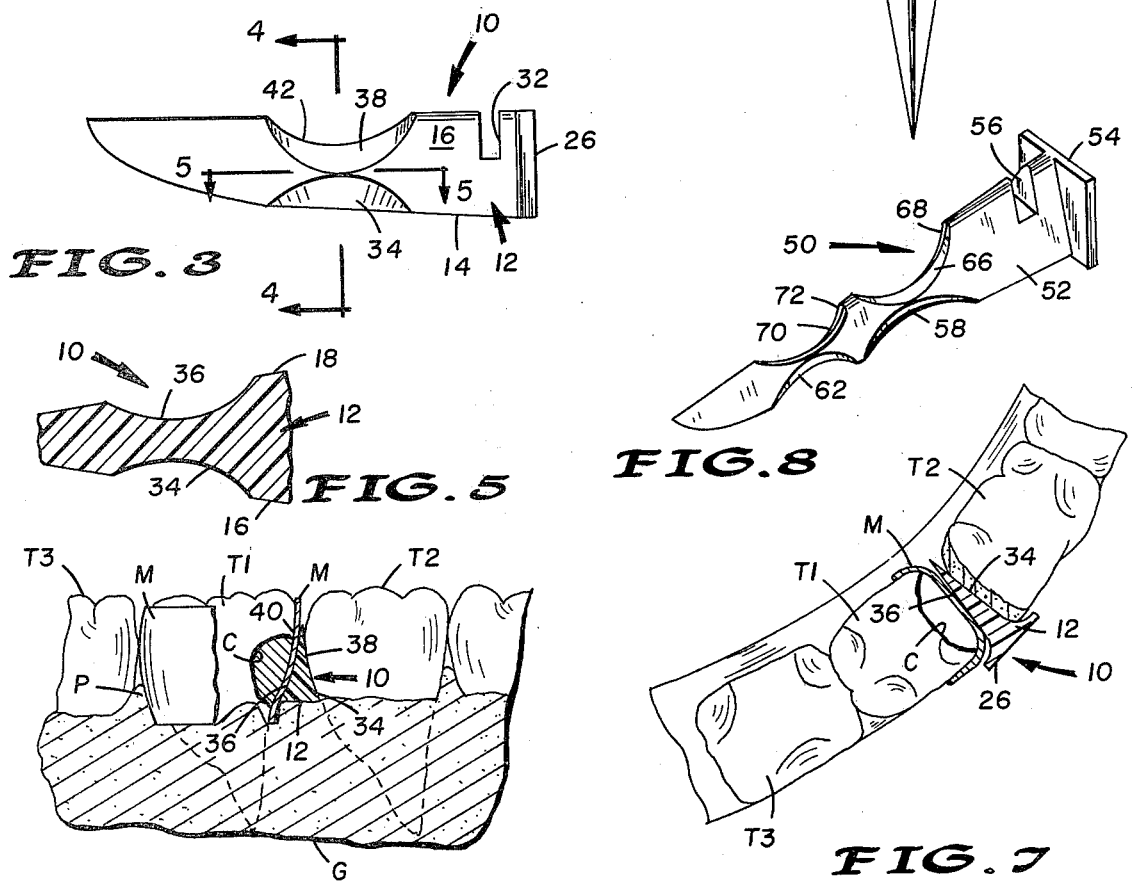

DENTAL WEDGE

BACKGROUND AND/OR ENVIRONMENT OF THE INVENTION

1. Field of the Invention

The present invention relates to dental wedges, and more particularly, to a dental wedge for interproximal disposition in the interdental space for fixing a matrix band or the like in position about a tooth in conjunction with a dental procedure.

2. Description of the Contemporary and/or Prior Art

In many instances, it is customary for a dentist to employ the aid of a matrix band about a tooth when forming fillings therein. The use of such a band presents two immediate problems. The band must be fixed in position, and also must be formed to the convex shape of the tooth so that a filling placed therein will conform anatomically to the outer surface of the healthy portion of the tooth.

Conventional dental wedges for the most part comprise tapered wood or plastic sticks which are inserted between the teeth with friction being relied upon to maintain these wedges in position. Such dental wedges are shown in U.S. Pat. Nos. 351,065 issued to Miller on Oct. 19, 1896; 2,567,101 issued to Carpenter on Sept. 4, 1951; 2,607,117 issued to Baughan on Aug. 19, 1952; 2,611,182 issued to Tofflemire on Sept. 23, 1952; and 3,262,208 issued to Johnson, Jr. on July 26, 1966. All of these dental wedges suffer from the same shortcomings. The wedges tend to slip out of position due to the demonstrably poor frictional engagement provided and also do not conform properly to the tapered outer surface of the adjacent teeth thereby limiting anatomic correctness of fillings inserted and shaped with their aid.

Solutions to these problems were and are sought in many different ways which include a modification of the wedge, band, or a combination thereof.

U.S. Pat. No. 532,722 issued to Dennis on Jan. 15, 1895 teaches a dental matrix which is held in position by a wedge that is taught to be expanding and has tapered sides with longitudinally extending concave grooves that are provided to permit this expansion. This improved shape enhances frictional engagement but does not provide the positive locking nor the anatomical contouring of the present invention.

U.S. Pat. No. 2,629,930 issued to Lane on Mar. 3, 1953 teaches a temporary wall for use in conjunction with the filling of dental cavities which includes a pair of complementary tapered elements that are placed on opposite sides of a band disposed in between adjacent teeth. This device requires manipulation on both the buccal and lingual sides of the teeth and also requires locking of a set screw in position for use, all of which significantly increases the manipulation required over the use of a conventional matrix band and a wedge.

U.S. Pat. Nos. 2,891,313 issued to Crowley on June 23, 1959; and 3,108,377 issued to Meyer on Oct. 29, 1963 each teach dental wedges which are tapered to eliminate the shortcomings of other prior art wedges. However, neither wedge teaches means for positively engaging and locking the wedge into position and mere friction is relied upon. Such is also the case with U.S. Pat. No. 2,782,503 issued to Thompson on Feb. 26, 1957. While Thompson and Meyer purport to conform to the contour of the outer surface of the teeth in between which these wedges are inserted, the actual conformity is minimal since the point of tangency between the curved surface of the tooth and the flat sides of these wedges are the only portions, if any, where any shaping approaching that of the tooth can take place.

Alternate approaches to solve these problems are shown in U.S. Pat. Nos. 3,795,052 issued to Mowery on Mar. 5, 1974; and 2,090,904 issued to Singer on Apr. 24, 1937. Mowery teaches a substantially flat matrix band which has a wedge portion fixedly secured thereto and Singer teaches a matrix which incorporates therein a wedge for insertion interproximally. Neither of these devices adequately simulate the contour of the tooth to be filled or provide means for positively locking these devices in position.

The present invention overcomes the aforenoted problems by providing a dental wedge which incorporates means for positively engaging the teeth between which it is inserted and for thereby locking the wedge therebetween. In addition, the present invention provides means for forming the matrix band which it is used in conjunction with to conform substantially to the anatomical contour of the tooth thereby simulating the concave and bulbous papilla of the gingiva.

SUMMARY OF THE INVENTION

Therefore, a primary object of the present invention is to provide a dental wedge for interproximal insertion in the interdental space which incorporates means for positively engaging the teeth it is inserted between and for locking the wedge in position.

A further object of the present invention is to provide a dental wedge for interproximal insertion in the interdental space which simulates the contour of the concave and bulbous papilla of the gingiva disposed in the interdental space so that anatomically correct fillings can be structured when the wedge is employed to fix the position of a matrix band.

Still another object of the present invention is to provide a dental wedge for interproximal insertion in the interdental space which incorporates means for facilitating the insertion and removal thereof.

Another still further object of the present invention is to provide a dental wedge for interproximal insertion in the interdental space which provides means for facilitating the gripping thereof by a cotton pliers or other dental gripping tool.

Still another further object of the present invention is to provide a dental wedge for interproximal insertion in the interdental space which can be manufactured so a single wedge can accommodate more than one interdental space size.

Another further object of the present invention is to provide a dental wedge for interproximal insertion in the interdental space which is ideally suited for manufacture using modern plastic formation techniques.

Still another further object of the present invention is to provide a dental wedge for interproximal insertion in the interdental space which, when employed, minimizes gingiva tissue damage.

Another still further object of the present invention is to provide a dental wedge for interproximal insertion in the interdental space which can be inserted with a minimum of effort.

An additional object of the present invention is to provide a dental wedge for interproximal insertion in the interdental space which is suitable for sterilization and therefore reuse.

Still another further object of the present invention is to provide a dental wedge for interproximal insertion in the interdental space which is simple in design, inexpensive to manufacture, rugged in construction, easy to use, and efficient in operation.

These objects, as well as further objects and advantages, of the present invention will become readily apparent after reading and ensuing description of the non-limiting illustrative embodiments and viewing the accompanying drawings.

A dental wedge for interproximal insertion in the interdental space between teeth according to the principles of the present invention includes an elongated body and means for positively engaging the teeth between which the wedge is inserted and for thereby locking the body therebetween.

BRIEF DESCRIPTION OF THE DRAWING

In order that the present invention may be more fully understood, it will now be described, by way of example, with reference to the accompanying drawings in which:

FIG. 1 is a pictorial representation in perspective of the dental wedge of the present invention incorporating the features thereof therein;

FIG. 2 is a top view of the dental wedge of FIG. 1;

FIG. 3 is a side view of the dental wedge of FIG. 1;

FIG. 4 is a cross-sectional view of the wedge of FIG. 1 taken substantially along the lines 4—4 of FIG. 3;

FIG. 5 is a fragmentary cross-sectional view of the dental wedge shown in FIG. 3 taken substantially along the lines 5—5 thereof;

FIG. 6 is a cross-sectional view of the dental wedge of the present invention inserted interproximally in the interdental space between two molars;

FIG. 7 is a partially broken away fragmentary cross-sectional view of the dental wedge and teeth shown in FIG. 6; and FIG. 8 is a pictorial representation of an alternate embodiment of the present invention.

DESCRIPTION OF THE PREFERRED EMBODIMENTS

Referring now to the figures, and more particularly to FIGS. 1, 2, 3, and 4 thereof, there is illustrated therein a dental wedge 10 incorporating the principles of the present invention therein. The dental wedge 10 includes an elongated body 12 which is substantially triangular in cross section and which includes a base portion 14 and side portions 16 and 18. The side portions 16 and 18 meet at a vertex edge 20 which forms the uppermost edge of the elongated body 12. The edge 20 may be configured as a line or as a rounded edge as illustrated. The elongated body 12 is configured to include an insertion end 22 and a manipulation end 24. The elongated body 12 is tapered along the longitudinal axis thereof so that the manipulation end 24 is substantially wider than the insertion end 22 as shown. Additionally, the base portion 14 is curved adjacent to the insertion end 22 with the base portion meeting the vertex edge 20 thereby giving the portion of the elongated body 12 adjacent to the insertion edge 22 a taper similar to that of the bow of a ship.

A head portion 26 is provided by the elongated body 12 and is substantially rectangular in shape. The head portion 26 is disposed so that the faces 28 and 30 thereof fall in planes which are substantially normal to the longitudinal axis of the elongated body 12 as illustrated in FIGS. 1, 2, and 3. The head portion 26 is provided to facilitate handling and insertion of the dental wedge 10 as hereinafter described. To facilitate engagement of the dental wedge 10 by a cotton pliers or other gripping dental tool, a notch 32 is disposed in the elongated body portion 12 adjacent to the head portion 26. Although the notch 32 is shown in a particular position in FIGS. 1, 2, and 3 of the drawing, other suitable positioning may be employed.

Keeping the aforegoing description in mind, it should be apparent that the present invention provides a wedge which can easily and quickly be inserted in between the teeth of a patient. In order to positively engage the teeth and to lock the wedge of the present invention between the teeth of the patient, a pair of depressions 34 and 36 are disposed, respectively, in the side portions 16 and 18 of the elongated body 12 adjacent to the base portion 14. The depressions 34 and 36 are tapered concavely to conform substantially to the interproximal surfaces of the teeth between which the dental wedge is to be disposed to fix a matrix band in position. It is realized that various size and types of teeth have different anatomical contours and the dental wedge 10 of the present invention would be provided in various sizes to accommodate these different sized teeth. Additionally, a multiple size wedge can be provided as discussed hereinafter in conjunction with FIG. 8.

Referring specifically to FIG. 5, it can be seen that the depressions 34 and 36 are concave in configuration. The depressions 34 and 36 are also disposed so that they present substantially mirror images of each other in the surfaces 16 and 18 although this may vary as necessary.

A pair of recesses 38 and 40 are disposed, respectively, in the side portions 16 and 18 adjacent to each other, with the recesses 38 and 40 merging together in an arcuate line 42 thereby undercutting the vertex edge 20 of the elongated body 12 formed by the sides 16 and 18 thereof. The recesses 38 and 40 are contoured as the papillia of the gingiva, which is disposed in the interdental space so that when the wedge 10 is inserted in between the teeth, the recesses 38 and 40 simulate the shape of the concave and bulbous papillia displaced thereby.

The recesses 38 and 40 are disposed in the elongated body 12 adjacent to the depressions 34 and 36 and are positioned relative to each other so that they can perform, respectively, contouring and locking functions simultaneously when inserted in the interdental space.

Referring to FIGS. 6 and 7, the dental wedge 10 is shown in use to fix a matrix band M around a tooth $T_1$ with the wedge 10 being inserted between teeth $T_1$ and teeth $T_2$. When the dental wedge 10 is inserted between the teeth $T_1$ and $T_2$, it displaces the concave and bulbous papillia in the interdental space. The papillia P of the gingiva G (commonly known as the gum) is illustrated between the tooth $T_1$ and tooth $T_3$. The shape of the papillia is simulated by recesses 38 and 40. Therefore, the matrix band M conforms substantially to the recess 40 so that a surface against which a filling placed in cavity C can conform to is provided so that the finished tooth $T_1$ has the correct anatomical contour. Simultaneously, the depressions 34 and 36 engage the side surfaces of the teeth $T_1$ and $T_2$ to effectively lock the elongated body 12 therebetween.

Entry of the wedge 10 into the interdental space is accomplished by the forcing of the insertion end 22 thereof between the teeth. This is accomplished through the placing of pressure on the head portion 26 of the wedge 10. Because of the taper of the elongated body 12 adjacent to the insertion end 22 thereof, the dental wedge 10 is easily interproximally positioned as shown in FIG. 7. When the depressions 34 and 36 align and conform substantially to the outer convex surfaces of the teeth between which the dental wedge 10 is inserted, the wedge 10 is locked in position. Additionally, this is accomplished without undue pressure on the adjacent teeth as would be caused if a wedge, not incorporating the depressions 34 and 36, and which relies on frictional engagement, was employed. After a cavity is filled and a matrix band is to be removed, the dental wedge 10 can be grasped in any suitable manner for withdrawal. To accommodate this operation, the notch 32 is provided so, for instance, the elongated body can be gripped by a cotton pliers or the like with a portion thereof being inserted in the notch 32.

Because of the simple configuration of the present invention, it may be inserted either from the buccal or lingual surface of the teeth, but it does not require manipulation at both these surfaces simultaneously. It should be apparent to one of ordinary skill in the art that a dental wedge employing the principles of the present invention could be constructed with only one locking depression with the opposed side of the wedge relying upon frictional engagement. Although this is not the preferred construction, it is within the scope of the present invention. Likewise, the dental wedge could also be constructed with a single recess for aiding in the contouring of the filling.

The dental wedge 10 can be constructed of a semi-resilient yieldable material so that the compression of the portion thereof adjacent to the insertion end 22 thereof is possible to facilitate positioning of the wedge 10. Suitable materials for the fabrication of the present invention include nylon, polyethylene, teflon, polypropylene, and other suitable materials.

It is contemplated that the dental wedge 10 would be constructed in various sizes to accommodate different sizes and types of teeth and differently dimensioned interdental spaces and that these various wedges would be color coded or otherwise marked to simplify identification. The wedge would be sterilizable and therefore reusable if proper materials in keeping with sound dental practice are employed.

To reduce the number of differently sized dental wedges which would be needed incorporating the principles of the present invention to accommodate all possible sizes of interdental spaces, a dental wedge similar to the dental wedge 50, as illustrated in FIG. 8, could be manufactured. Dental wedge 50 includes an elongated body 52 which is tapered essentially as elongated body 12 of dental wedge 10. Dental wedge 50 includes a head portion 54 similar to head portion 26 of dental wedge 10 and a notch 56 correspondingly similar to notch 32. Dental wedge 50 includes two pairs of depressions 58 and 60 (60 not illustrated) and 62 and 64 (64 not illustrated). The pairs of depressions 58 and 60 and 62 and 64 are similar to the depressions 34 and 36 of dental wedge 10, but are different in size so that the dental wedge 50 can be used in a relatively narrow interdental space with the teeth forming the interdental space being engaged by depressions 62 and 64 or in a relatively wider interdental space with the teeth being engaged by depressions 58 and 60. As the recesses 38 and 40 are provided in dental wedge 10, similarly recesses 66 and 68 and 70 and 72 are provided to simulate the contour of the outer surface of the teeth to position a matrix band so that the filling placed in a cavity in a tooth surrounded by a matrix band can be contoured in an anatomically correct manner. It should be apparent to one of ordinary skill in the art that a dental wedge including several sets of depressions and recesses for, respectively, positively engaging and locking between teeth and for contouring to these teeth for the construction thereof can be provided thereby limiting the number of different sizes of dental wedges required.

It will be understood that various changes in the details, materials, and arrangements of the parts and operational conditions which have been herein described and illustrated in order to explain the nature of the invention, may be made by those skilled in the art within the principles and scope of the present invention.

Having thus set forth the nature of the invention, what is claimed is:

1. A unitary dental wedge for interproximal insertion in the interdental space between teeth comprising:
an elongated body being substantially triangular in cross section;
means for positively engaging said teeth thereby locking said body therebetween, said positive engagement and locking means comprising at least one depression disposed in a portion of said elongated body contacting one of said teeth when said body is interproximally disposed, said depression being concavely tapered to conform substantially to and for capturing and selectively retaining therein a part of said contacted portion of said tooth, said contacted portion of said tooth being an interproximal surface thereof, said at least one depression being contoured to substantially conform to said contacted interproximal surface; and
means for simulating the contour of the concave bulbous papillia of the gingiva disposed in the interdental space when said papillia is displaced by interproximal insertion of said dental wedge, said contour simulating means comprising a pair of recesses disposed in said elongated body, said recesses being contoured as said papillia, said elongated body portion including a pair of side portions meeting at a vertex edge and a base portion, one of said recesses being disposed in one of said sidewalls, the other of said recesses being disposed in the other of said sidewalls, said recesses being adjacent, merging together, and undercutting said vertex edge proximate thereto.

2. A dental wedge in accordance with claim 1, wherein said elongated body is tapered along the longitudinal axis thereof.

3. A dental wedge in accordance with claim 1, wherein said at least one depression comprises at least one pair of depressions, said elongated body including a pair of side portions and a base portion, one of said depressions of each of said pairs being disposed in one of said side portions, the other of said depressions being disposed in the other of said side portions.

4. A dental wedge in accordance with claim 3, wherein each of said depressions are disposed in said side portions adjacent to said base portion.

5. A dental wedge in accordance with claim 1, wherein a pair of said recesses are disposed in said elongated body adjacent each said at least one depression or cooperating pair thereof disposed in said elongated body.

6. A dental wedge in accordance with claim 2, wherein said elongated body is tapered from an insertion end to a wider manipulation end, said elongated body further comprising a head portion adjacent to said manipulation end to facilitate interproximal insertion and handling of said dental wedge.

7. A dental wedge in accordance with claim 6, wherein said head portion is substantially rectangular, said longitudinal axis of said elongated body being substantially normal to the planes in which the faces of said head portion are disposed.

8. A dental wedge in accordance with claim 2, wherein said elongated body portion is tapered from an insertion end to a wider manipulation end, said elongated body portion comprising a pair of side portions meeting at a vertex edge and a base portion, said base portion being curved adjacent to the insertion end of said elongated body, said base portion meeting said vertex edge at a point at said insertion end.

9. A dental wedge in accordance with claim 6, further comprising means to facilitate the engagement of said elongated body by a gripping dental instrument.

10. A dental wedge in accordance with claim 9, wherein said engagement facilitation means comprises a notch disposed in said elongated body adjacent to said head portion thereof.

11. A dental wedge in accordance with claim 1, wherein said elongated body is formed from a semi-resilient material.

12. A dental wedge in accordance with claim 11, wherein said dental wedge is formed as an integral unitary body.

* * * * *